(12) United States Patent
Bae et al.

(10) Patent No.: US 8,964,015 B2
(45) Date of Patent: Feb. 24, 2015

(54) SYSTEM AND METHOD FOR CHECKING STATE OF ROTATOR

(75) Inventors: Su-bong Bae, Suwon-si (KR); Chung-ung Kim, Yongin-si (KR); Ki-ju Lee, Suwon-si (KR); Jong-jin Park, Yongin-si (KR); Dong-hwi Cho, Suwon-si (KR); Jong-cheol Kim, Suwon-si (KR)

(73) Assignee: Samsung Electronics Co., Ltd., Suwon-Si (KR)

(*) Notice: Subject to any disclaimer, the term of this patent is extended or adjusted under 35 U.S.C. 154(b) by 738 days.

(21) Appl. No.: 12/731,726

(22) Filed: Mar. 25, 2010

(65) Prior Publication Data

US 2010/0253771 A1   Oct. 7, 2010

(30) Foreign Application Priority Data

Apr. 3, 2009   (KR) .................. 10-2009-0029059

(51) Int. Cl.
   *H04N 7/18*   (2006.01)
   *B04B 13/00*   (2006.01)
   *G01N 21/952*   (2006.01)

(52) U.S. Cl.
   CPC .............. *B04B 13/00* (2013.01); *G01N 21/952* (2013.01)
   USPC ............................................. 348/61; 348/94

(58) Field of Classification Search
   CPC ......... G01S 19/42; G01S 19/48; G01S 19/51; G01S 5/0009; G01S 5/0263; G01S 5/0268; G01S 5/0284; G01S 5/16; G01S 5/0252; H04N 5/222; H04N 5/232; H04N 5/228; A61B 10/0045; B23Q 17/22; G06F 3/0425; G06K 9/20; B04B 13/00; G01N 21/952

USPC ....................................................... 348/61, 94
See application file for complete search history.

(56) References Cited

U.S. PATENT DOCUMENTS

| 7,088,650 | B1 | 8/2006 | Worthington et al. |
| 7,221,632 | B2 | 5/2007 | Worthington |
| 7,396,324 | B2* | 7/2008 | Tetsu et al. ........... 494/7 |
| 2005/0272993 | A1* | 12/2005 | Ishii ................ 600/407 |
| 2006/0065839 | A1* | 3/2006 | Wagenaar et al. ....... 250/363.05 |
| 2009/0274348 | A1* | 11/2009 | Jakubowicz et al. ......... 382/128 |

FOREIGN PATENT DOCUMENTS

| EP | 1 324 042 A2 | 7/2003 |
| JP | 63-302367 | 12/1988 |

* cited by examiner

*Primary Examiner* — Alina N Boutah
(74) *Attorney, Agent, or Firm* — Staas & Halsey LLP (57) ABSTRACT

Provided are a system and method for checking a state of a rotator. The system includes: a position recognition sensor that senses a position of a rotator and generates a position synchronization signal corresponding to the position of the rotator; a control unit that detects a position of a detection specimen existing in the rotator based on the position synchronization signal and generates an image photographing control signal corresponding to the detected position of the detection specimen; and a camera system that photographs an image of the detection specimen existing in the rotator based on the image photographing control signal. Accordingly, movement of a detection specimen existing in the rotator when the rotator stops rotating or whether a detection specimen being rotated is centrifuged, moved, or dried is monitored and controlled, thereby checking a change in a state of the detection specimen in the process of development of the rotator and checking whether each of operations of the system is completed.

17 Claims, 11 Drawing Sheets

SYSTEM AND METHOD FOR CHECKING STATE OF ROTATOR

CROSS-REFERENCE TO RELATED APPLICATIONS

This application claims the benefit of Korean Patent Application No. 10-2009-0029059, filed on Apr. 3, 2009, in the Korean Intellectual Property Office, the disclosure of which is incorporated herein in its entirety by reference.

BACKGROUND

An embodiment relates to a system and method for checking a state of a rotator, and more particularly, to a system and method for checking a state of a rotator by using a position synchronization signal and/or a rotational speed synchronization signal.

In a conventional system for checking a state of a rotator, while a material to be detected, e.g., blood, which is included in the rotator, is being rotated, it cannot be verified whether centrifuging of the material is completed, whether the material is moved to a predetermined position, or whether an operation of drying the material is completed. Accordingly, every operation conducted in the system for checking a state of a rotator needs to be controlled by a time setting. Thus, the system is not capable of controlling the rotator until the setting of the time is finished.

SUMMARY

Additional aspects and/or advantages will be set forth in part in the description which follows and, in part, will be apparent from the description, or may be learned by practice of the invention.

The embodiment provides a system and/or method for checking a state of a rotator, wherein a position synchronization signal and/or a rotational speed synchronization signal are used to monitor: movement state of a detection specimen existing in the rotator when the rotator stops rotating; a centrifugal condition, a movement state, or a drying condition of a detection specimen being rotated; or an operation of the system.

According to an aspect a system for checking a state of a rotator, including: a position recognition sensor that senses a position of a rotator and generates a position synchronization signal corresponding to the position of the rotator; a control unit that detects a position of a detection specimen existing in the rotator based on the position synchronization signal and generates an image capturing control signal corresponding to the detected position of the detection specimen; and a camera system that captures an image of the detection specimen existing in the rotator based on the image capturing control signal is provided.

The system may further include a rotational speed synchronization signal generating unit that generates a rotational speed synchronization signal having a frequency in proportion to a rotational speed of the rotator, wherein the control unit detects a position and a rotational speed of a detection specimen existing in the rotator based on the position synchronization signal and the rotational speed synchronization signal and generates an image capturing control signal corresponding to the detected position and the detected rotational speed of the detection specimen.

The camera system may include: an illumination unit that emits light to the detection specimen; a camera module that captures an image of the detection specimen; an instrument unit that fixes the camera module; a supporting unit, to which the instrument unit is connected so that the instrument unit is capable of sliding in a diameter direction of the rotator; and a feeding motor that transmits motive power to the instrument unit to move the instrument unit.

At least one chamber, in which a detection specimen is stored, may be disposed on a surface of the rotator and a recognition mark that displays data of the chamber is respectively attached on the surface of the rotator, and the position recognition sensor senses the recognition mark to generate the position synchronization signal.

The position recognition sensor may include a light emitting unit and a light receiving unit, and the light emitting unit emits light to the recognition mark, and the light receiving unit may receive the light that is either reflected by or transmitted through the recognition mark to generate the position synchronization signal.

The light emitting unit and the light receiving unit may be disposed below the rotator and generate the position synchronization signal corresponding to an amount of reflected light.

The light emitting unit and the light receiving unit may be disposed opposite each other, having the rotator interposed therebetween, and generate the position synchronization signal corresponding to an amount of transmitted light.

The light emitting unit may be one of an infrared ray sensor, a light emitting diode (LED), and a laser, and the light receiving unit is a photo-detector.

The recognition mark may include at least a mark representing an initial start position of the chamber.

The recognition mark may include at least a mark that represents an image capturing position.

The recognition mark may include at least a mark that represents a chamber type.

According to another aspect a method of checking a state of a rotator, the method including: sensing a position within a rotator and generating a position synchronization signal corresponding to the position within the rotator; generating a rotational speed synchronization signal having a frequency in proportion to a rotational speed of the rotator; detecting a position and a rotational speed of a detection specimen existing in the rotator based on the position synchronization signal and the rotational speed synchronization signal; and capturing an image of the detection specimen existing in the rotator based on results of the detecting is provided.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF EMBODIMENTS

Reference will now be made in detail to the embodiments, examples of which are illustrated in the accompanying drawings, wherein like reference numerals refer to the like elements throughout. The embodiments are described below to explain the present invention by referring to the figures.

The attached drawings for illustrating embodiments of the inventive concept are referred to in order to gain a sufficient understanding of the inventive concept, the merits thereof, and the objectives accomplished by the implementation of the inventive concept.

Hereinafter, the embodiment will be described in detail by explaining preferred embodiments of the inventive concept with reference to the attached drawings. Like reference numerals in the drawings denote like elements.

The embodiment relates to a system for checking a state of a detection specimen that is included in a rotator, and particularly, to monitoring a state of a detection specimen, such as blood, that is disposed in a predetermined chamber of a bio disc that is used as a rotator, or to any technology that may use the state of the detection specimen as a feedback signal. The rotator in embodiments of the inventive concept is not limited to a bio disc but may be any rotator including therein a specimen at a predetermined position, for checking the state of the specimen.

Figure 1:
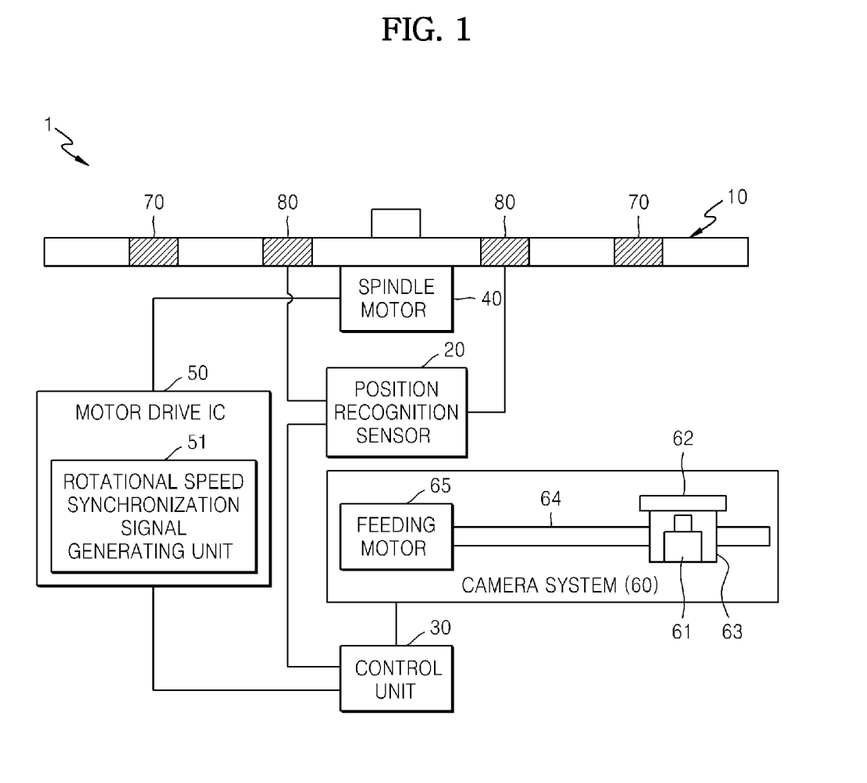
FIG. 1 is a schematic view illustrating a system for checking a state of a rotator according to an embodiment.
Figure 2:
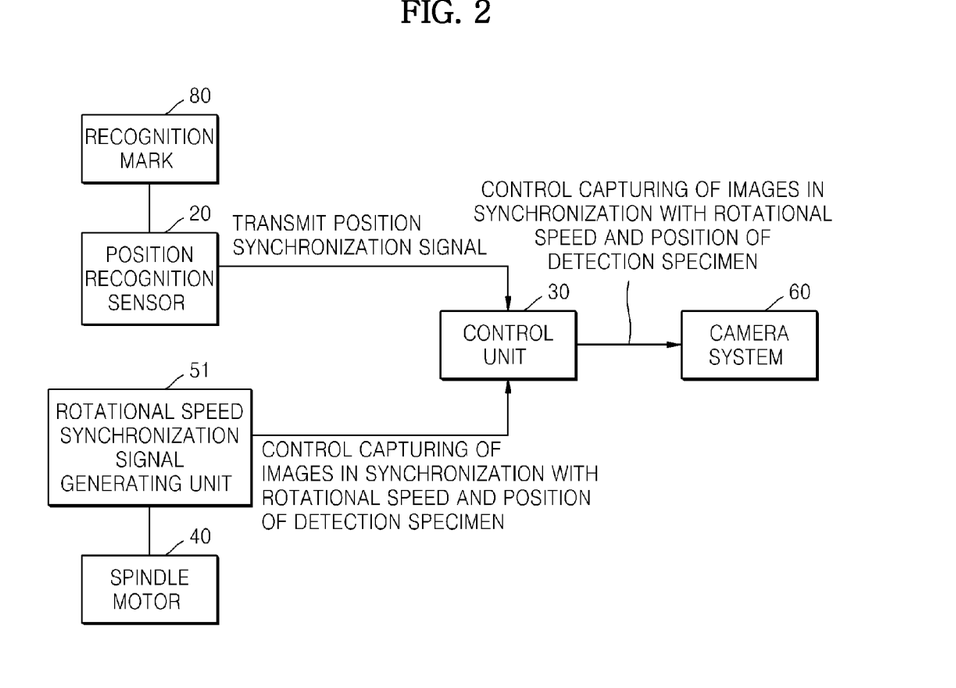
FIG. 2 is a block diagram illustrating a system for checking a state of a rotator according to an embodiment.

FIG. 1 is a schematic view illustrating a rotator state checking system 1 according to an embodiment, and FIG. 2 is a block diagram illustrating a rotator state checking system for checking a state of a rotator according to an embodiment.

The rotator state checking system 1 detects a position and a rotational speed of a detection specimen in a rotator 10 based on a position synchronization signal and a rotational speed synchronization signal, and allows a photographic image to be taken of the detection specimen in the rotator 10 based on the detected position and the detected rotational speed thereof.

The rotator state checking system 1 includes a chamber 70 in which the detection specimen is stored, the rotator 10 including a recognition mark 80 for recognizing the chamber 70, and a spindle motor 40 that is capable of mounting the rotator 10 and rotating the same at high speed.

A position recognition sensor 20 that generates a position synchronization signal to adjust synchronization with a predetermined position of the detection specimen is associated with the rotator 10. In detail, at least one chamber 70 in which a detection specimen is stored and at least one recognition mark 80 marking data of the chamber 70 are disposed on a surface of the rotator 10, and the position recognition sensor 20 senses the recognition mark 80 attached to the rotator 10, to generate a position synchronization signal.

A control unit 30 receives the position synchronization signal generated by the position recognition sensor 20, and detects a position of the detection specimen existing in the rotator 10 based on the received position synchronization signal. Also, the control unit 30 generates an image photographing control signal corresponding to the detected position of the detection specimen so that a camera system 60 is synchronized with a predetermined position of the rotator 10, and the camera captures an image of the detection specimen existing at the predetermined position of the rotator 10.

The control unit 30 may be a micro-controller.

The rotator state checking system 1 according to the embodiment of the inventive concept further includes a rotational speed synchronization signal generating unit 51 included in a motor drive integrated circuit (IC) 50, which generates a rotational speed synchronization signal for synchronizing with the rotational speed of the rotator 10.

The rotational speed synchronization signal generating unit 51 generates a rotational speed synchronization signal having a frequency in proportion to a rotational speed of the rotator 10.

The control unit 30 receives the rotational speed synchronization signal that is generated by the rotational speed synchronization signal generating unit 51 and detects a rotational speed of the detection specimen existing in the rotator 10 based on the received rotational speed synchronization signal.

Also, the control unit 30 generates an image photographing control signal corresponding to the detected rotational speed of the rotator 10 so that the camera system 60 is synchronized with the rotational speed of the rotator 10 and the camera captures an image of the detection specimen existing at a predetermined position of the rotator 10.

In detail, the motor drive IC 50 controls the rotational speed of the rotator 10 by controlling the spindle motor 40, and the rotational speed synchronization signal generating unit 51 generates a rotational speed synchronization signal from the rotational speed of the rotator 10 and transmits the same to the control unit 30. The control unit 30 detects a rotational speed of a detection specimen based on the received rotational speed synchronization signal and generates an image photographing signal corresponding to the detected rotational speed of the detection specimen and controls the camera system 60 to capture several images per rotation of the rotator 10 according to the performance of the camera system 60.

By repeating the above operations, changes in the state of the detection specimen included in the rotator 10, which is being rotated, may be automatically monitored over time.

The camera system 60 used in the rotator state checking system 1 captures an image of the detection specimen disposed at a predetermined position, and includes a camera module 61, an illumination unit 62, an instrument unit 63, a supporting unit 64, and a feeding motor 65.

The illumination unit 62 emits light to or toward a detection specimen, and the camera module 61 captures an image of the detection specimen by using light that is reflected by or transmitted through the detection specimen. The camera module 61 needs to photograph the detection specimen included in the rotator 10 while the rotator 10 is rotating, and thus requires a high performance photographing method. Examples of the camera module 61 include a complementary metal-oxide semiconductor (CMOS) camera, a charge-coupled device (CCD) camera, and other various types of camera modules.

The instrument unit 63 is used to fix the camera module 61. The instrument unit 63 may be connected to the supporting unit 64 and to slide in a radial direction of the rotator 10. Meanwhile, the feeding motor 65 transmits motive power to the instrument unit 63 so that the instrument unit 63 including the camera module 61 can move to the chamber 70 in which the detection specimen to be photographed is positioned.

As described above, the camera module 61 is not fixedly positioned but is capable of moving in the diameter direction of the rotator 10, and thus the control unit 30 controls the camera system 60 to be synchronized with a position synchronization signal and/or a rotational speed synchronization signal of the rotator 10 and thus captures an image of the detection specimen that is being rotating at a predetermined position of the rotator 10 at a particular rotational speed.

Accordingly, the rotator state checking system 1 according to the embodiment may monitor movement conditions of the detection specimen included in the chamber 70 of the rotator 10 or various states of the detection specimen while the rotator 10 is rotating, thereby checking whether each of the operations performed on the detection specimen is completed and how the detection specimen is changed. Also, according to the current embodiment of the inventive concept, a rotational speed synchronization signal and a position synchronization signal are received, and thus images of a plurality of detection specimens included in the rotator 10 at the predetermined position are photographed in automatic synchronization with a speed of the rotator 10.

Figure 3:
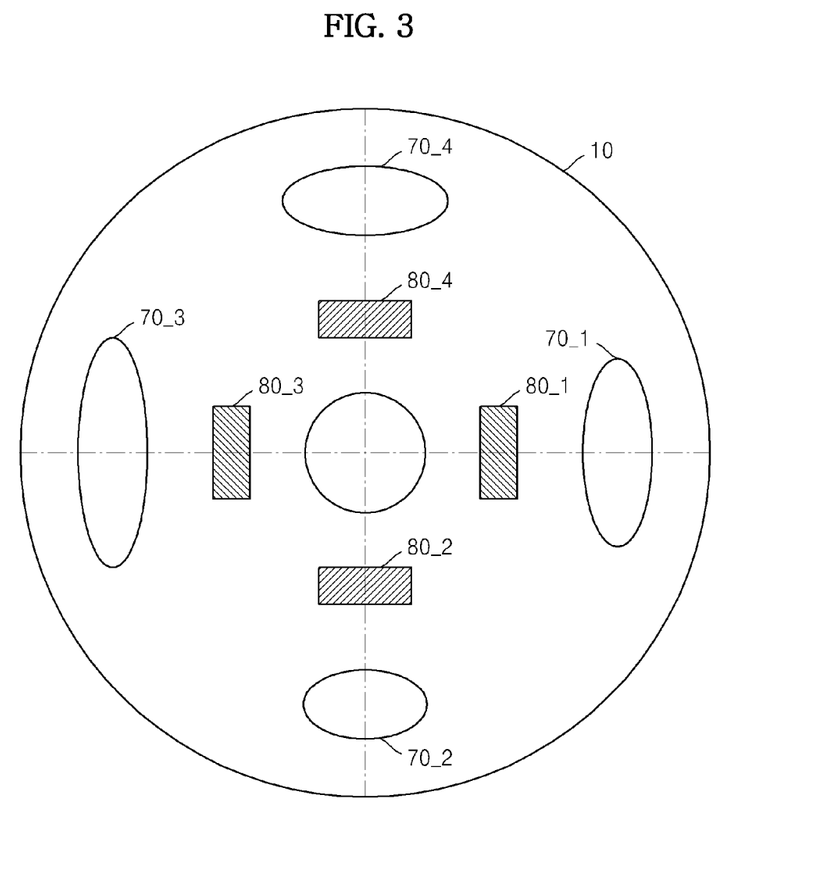
FIG. 3 is a plan view illustrating a rotator used in a system for checking a state of a rotator according to an embodiment.

FIG. 3 is a plan view illustrating a rotator 10 used in a system for checking a state of a rotator according to an embodiment of the inventive concept.

One or more chambers, in each of which a detection specimen is stored, are disposed on or in a surface of the rotator 10, and a recognition mark representing each of the chambers may be respectively attached. In FIG. 3, four first through fourth chambers 70_1, 70_2, 70_3, and 70_4 are disposed on the rotator 10, but more chambers may also be disposed.

Different detection specimens are respectively included in the first chamber 70_1, the second chamber 70_2, the third chamber 70_3, and the fourth chamber 70_4. Thus, when a user wants to check a state of a detection specimen in one of the plurality of chambers, the chamber needs to be identified.

As illustrated in FIG. 3, the first chamber 70_1, the second chamber 70_2, the third chamber 70_3, and the fourth chamber 70_4 are formed on the rotator 10, and a first recognition mark 80_1, a second recognition mark 80_2, a third recognition mark 80_3, and a fourth recognition mark 80_4 are respectively positioned between the first through fourth chambers 70_1, 70_2, 70_3, and 70_4 and a center of the rotator 10.

Meanwhile, a position recognition sensor senses the first through fourth recognition marks 80_1, 80_2, 80_3, and 80_4 included in the rotator 10 to generate a position synchronization signal of a predetermined chamber in which a detection specimen to be detected exists. Hereinafter, a method of generating a signal by using the position recognition sensor by sensing a recognition mark will be described.

Figure 4A:
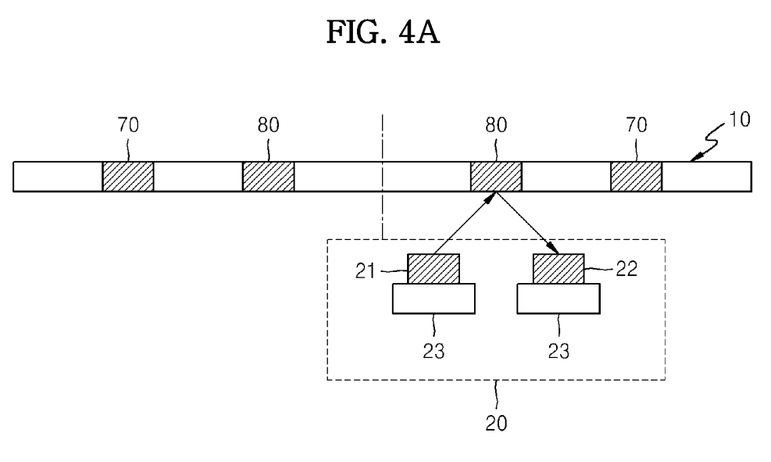
FIGS. 4A and 4B are cross-sectional views of a position of a chamber included in a rotator that is recognized by using a light emitting unit and a light receiving unit of a position recognition sensor which are disposed below the rotator by using reflected light, according to an embodiment.
Figure 4B:
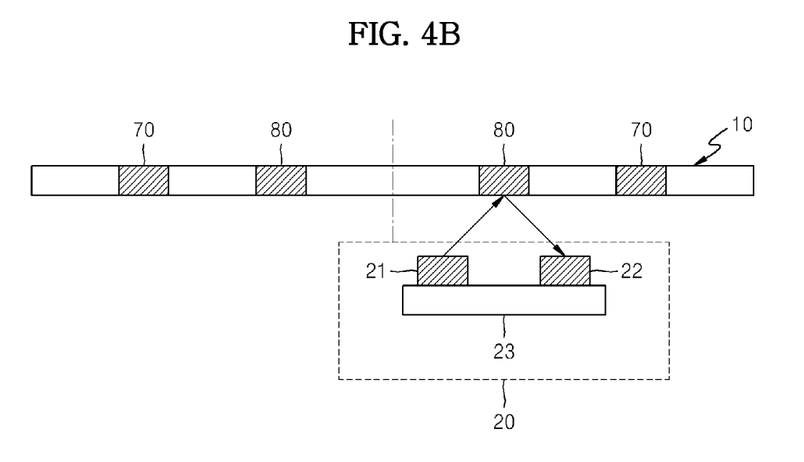

FIGS. 4A and 4B are cross-sectional views for explaining recognition of a position of a chamber included in a rotator that is recognized by using a light emitting unit and a light receiving unit of a position recognition sensor, which are disposed below the rotator, by using reflected light, according to an embodiment of the inventive concept.

The position recognition sensor 20 includes a light emitting unit 21 and a light receiving unit 22.

The light emitting unit 21 emits light to or toward a recognition mark 80 of a rotator 10, and the light receiving unit 22 receives the light emitted to and reflected by the recognition mark 80 to generate a position synchronization signal.

The light emitting unit 21 and the light receiving unit 22 may be disposed below the rotator 10. In other words, the light emitted by the light emitting unit 21 to the recognition mark 80 may be reflected, and the light receiving unit 22 may receive the reflected light to generate a position synchronization signal corresponding to the recognition mark 80. Meanwhile, the light emitting unit 21 and the light receiving unit 22 may be disposed on different printed circuit boards (PCBs) 23 as illustrated in FIG. 4A or on one PCB 23 as illustrated in FIG. 4B.

The light emitting unit 21 may preferably be one of an infrared ray emitter, a light emitting diode (LED), and a laser. The light receiving unit 22 may be a photo-detector.

Figure 5A:
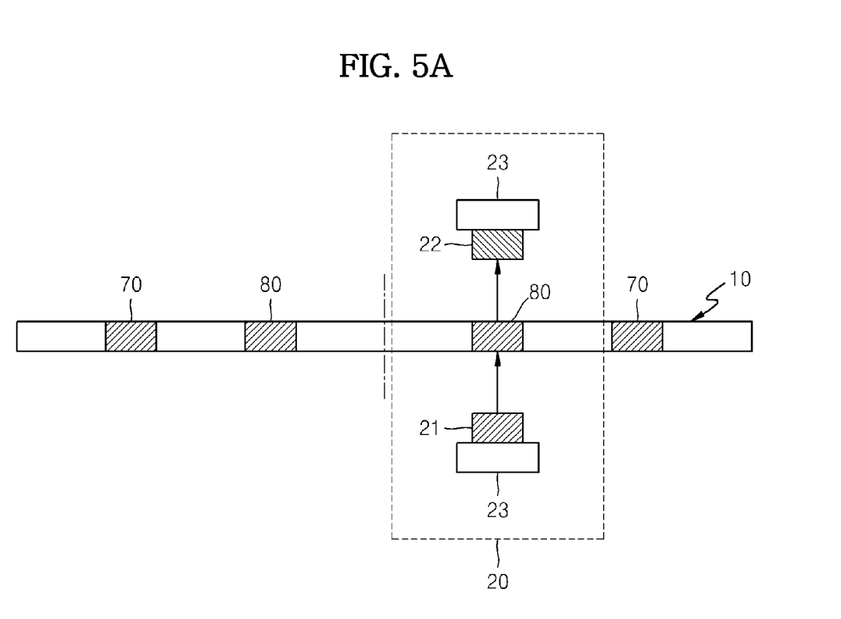
FIGS. 5A and 5B are cross-sectional views of a position of a chamber included in a rotator that is recognized by using transmitted light, wherein the rotator is disposed between a light emitting unit and a receiving unit of a position recognition sensor in a symmetrical configuration, according to an embodiment.
Figure 5B:
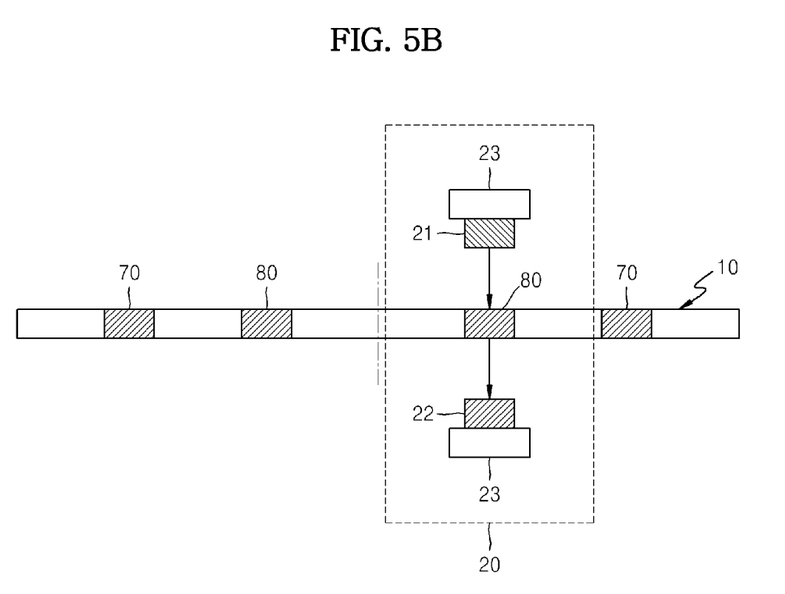

FIGS. 5A and 5B are cross-sectional views illustrating a position of a chamber included in a rotator 10 that is recognized by using transmitted light, wherein the rotator is disposed between a light emitting unit 21 and a light receiving unit 22 of a position recognition sensor 20 in a symmetrical configuration, according to an embodiment of the inventive concept.

As illustrated in FIGS. 5A and 5B, the light emitting unit 21 and the light receiving unit 22 may be disposed opposite each other while having a rotator 10 disposed therebetween. That is, light emitted by the light emitting unit 21 to a recognition mark 80 may be transmitted through the recognition mark 80, and the light receiving unit 22 may receive the transmitted light to generate a position synchronization signal of a chamber 70 corresponding to the recognition mark 80.

Meanwhile, the light emitting unit 21 may be disposed below the rotator 10 and the light receiving unit 22 may be disposed above the rotator 10 as illustrated in FIG. 5A, or the light emitting unit 21 may be disposed above the rotator 10 and the light receiving unit 22 may be disposed below the rotator 10 as illustrated in FIG. 5B.

Figure 6:
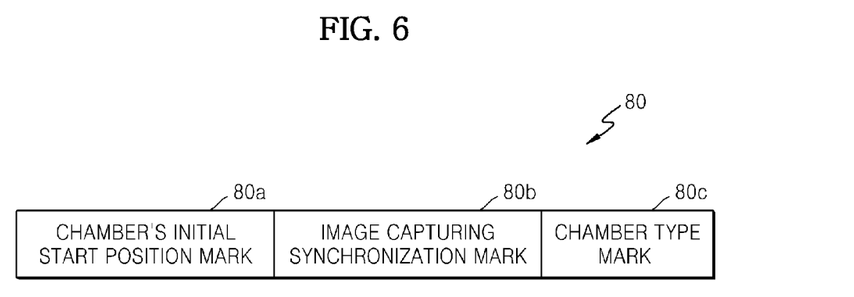
FIG. 6 is a structural diagram of a recognition mark included in a rotator, according to an embodiment.

FIG. 6 is a structural diagram of a recognition mark 80 included in a rotator 10, according to an embodiment of the inventive concept.

The recognition mark 80 includes a chamber's initial start position mark 80a, an image photographing synchronization mark 80b, and a chamber type mark 80c.

The chamber's initial start position mark 80a represents an initial start position of a predetermined chamber. The position recognition sensor 20 senses an initial start position of a predetermined chamber provided by the chamber's initial start position mark 80a to generate an initial chamber start signal. The initial chamber start signal is transmitted to the control unit 30, and the control unit 30 may control the camera system 60 to prepare for capturing of an image of a detection specimen included in a predetermined chamber.

The image capturing synchronization mark 80b represents an image capturing position of a predetermined chamber.

The position recognition sensor 20 senses an image capturing position of a predetermined chamber provided by the image capturing synchronization mark 80b to generate a position synchronization signal. The position synchronization signal is transmitted to the control unit 30, and the control unit 30 synchronizes the camera system 60 with a position of the image capturing synchronization mark 80b included for the predetermined chamber so that the camera may capture an image of the detection specimen included in the predetermined chamber.

The chamber type mark 80c represents a type of a predetermined chamber, which is used to identify a plurality of chambers.

The position recognition sensor 20 senses a chamber type indication provided by the chamber type mark 80c to generate a chamber type signal. The chamber type signal is transmitted to the control unit 30. The control unit 30 may control the camera system 60 such that the camera system 60 identifies a predetermined chamber to be photographed and captures an image of the detection specimen included in the predetermined chamber.

In addition, the chamber type mark 80c may be used after the camera system 60 finishes capturing images, when the user analyzes the photographed image, to check, among a plurality of captured images, the chamber in which the detection specimen exists and a state of the detection specimen existing in the chamber.

Figure 7A:
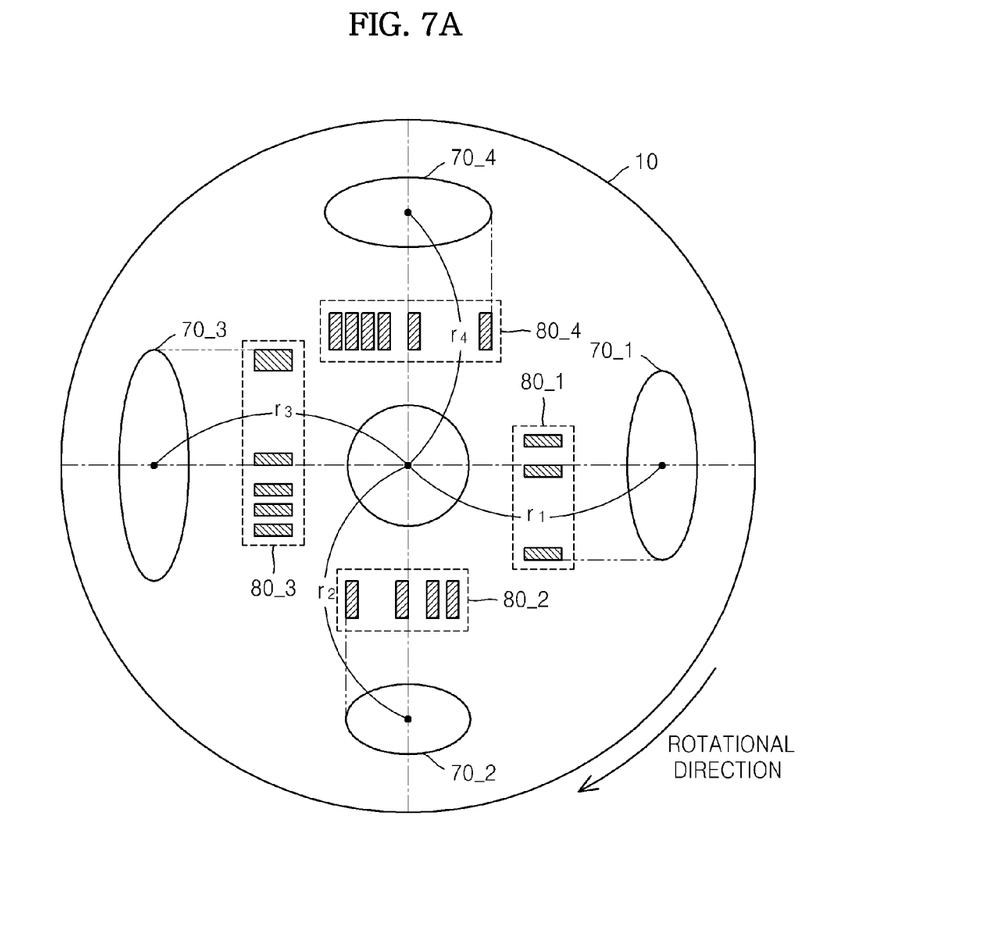
FIG. 7A is a plan view illustrating a chamber and a recognition mark disposed in a rotator used in a system for checking a state of a rotator, according to an embodiment.
Figure 7B:
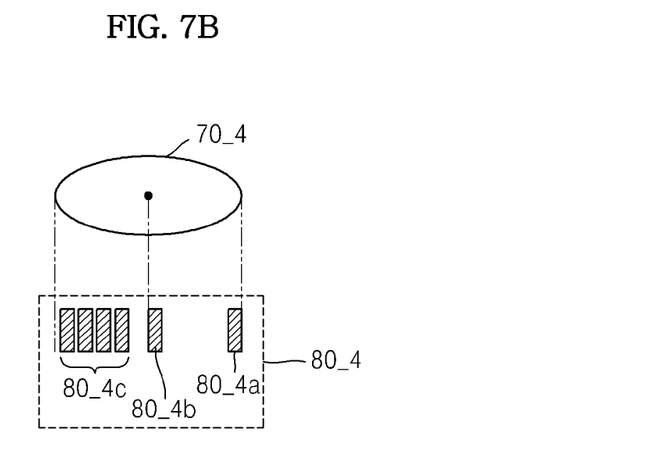
FIG. 7B is an extended view of a fourth chamber and a fourth recognition mark illustrated in FIG. 7A.

FIG. 7A is a plan view of a plurality of chambers and recognition marks disposed in a rotator 10 used in a rotator state checking system, according to an embodiment of the inventive concept, and FIG. 7B is an extended view of a fourth chamber and a fourth recognition mark illustrated in FIG. 7A.

The rotator 10 may include a plurality of chambers, and different detection specimens may exist in the chambers.

Referring to FIG. 7A, recognition marks in the form of recognition bars are attached to the rotator 10. In detail, a first chamber 70_1, a second chamber 70_2, a third chamber 70_3, and a fourth chamber 70_4 are respectively formed radial distances r1, r2, r3, and r4 away from a center of the rotator 10. The recognition marks are attached between the first through fourth chambers 70_1, 70_2, 70_3, and 70_4 and the center of the rotator 10. A first recognition mark 80_1 for the first chamber 70_1, a second recognition mark 80_2 for the second chamber 70_2, a third recognition mark 80_3 for the third chamber 70_3, and a fourth recognition mark 80_4 for the fourth chamber 70_4 are respectively attached.

Referring to FIG. 7B, an extended view of the fourth recognition mark 80_4 for the fourth chamber 70_4 is illustrated, wherein the fourth recognition mark 80_4 includes recognition bars, according to an embodiment of the inventive concept.

A chamber's initial start position mark 80_4a of the fourth recognition mark 80_4 marks a position where the fourth chamber 70_4 is started, and a position recognition sensor 20 generates an initial chamber start signal as the chamber's initial start position mark 80_4a senses an initial start position of the fourth chamber 70_4. The initial chamber start signal is transmitted to a control unit 30, and the control unit 30 controls a camera system 60 to prepare photographing of a detection specimen included in the fourth chamber 70_4.

An image capturing synchronization mark 80_4b of the fourth recognition mark 80_4 marks an image capturing position of the fourth chamber 70_4, and the position recognition sensor 20 senses the image capturing position of the fourth chamber 70_4 provided by the image capturing synchronization mark 80_4b to generate a position synchronization signal. The position synchronization signal is transmitted to the control unit 30, and the control unit 30 synchronizes the camera system 60 with a position of an image capturing synchronization mark 80_4b included in the fourth chamber 70_4 to capture an image of the detection specimen included in the predetermined chamber.

A chamber type mark 80_4c of the fourth recognition mark 80_4 includes four recognition bars arranged in a row. In detail, four recognition bars are arranged to identify the fourth chamber 70_4. Referring to FIG. 7A again, a chamber type mark 80_1c of the first chamber 70_1 includes only one recognition bar, a chamber type mark 80_2c of the second chamber 70_2 includes two recognition bars arranged in a row, and a chamber type mark 80_3c of the third chamber 70_3 includes three recognition bars arranged in a row.

The chamber type mark 80_4c of the fourth recognition mark 80_4 indicates a type of the fourth chamber 70_4 and is used to distinguish the fourth chamber 70_4 from the first chamber 70_1, the second chamber 70_2, and the third chamber 70_3.

The position recognition sensor 20 senses a chamber type indication provided by the chamber type mark 80_4c to generate a chamber type signal of the fourth chamber 70_4. The chamber type signal is transmitted to the control unit 30. The control unit 30 controls the camera system 60 such that the camera system 60 identifies the fourth chamber 70_4 that is to be photographed and captures an image of the detection specimen included in the predetermined chamber.

The recognition mark 80 may be arranged in the rotator 10 in various ways, and the arrangements illustrated in FIGS. 7A and 7B may also be modified in other various forms.

Also, as described above, the fourth recognition mark 80_4 of the fourth chamber 70_4 includes recognition bars, and so may be the first recognition mark 80_1 of the first chamber 70_1, the second recognition mark 80_2 of the second chamber 70_2, and the third recognition mark 80_3 of the third chamber 70_3. Herein, detailed descriptions thereof will be omitted.

Figure 8:
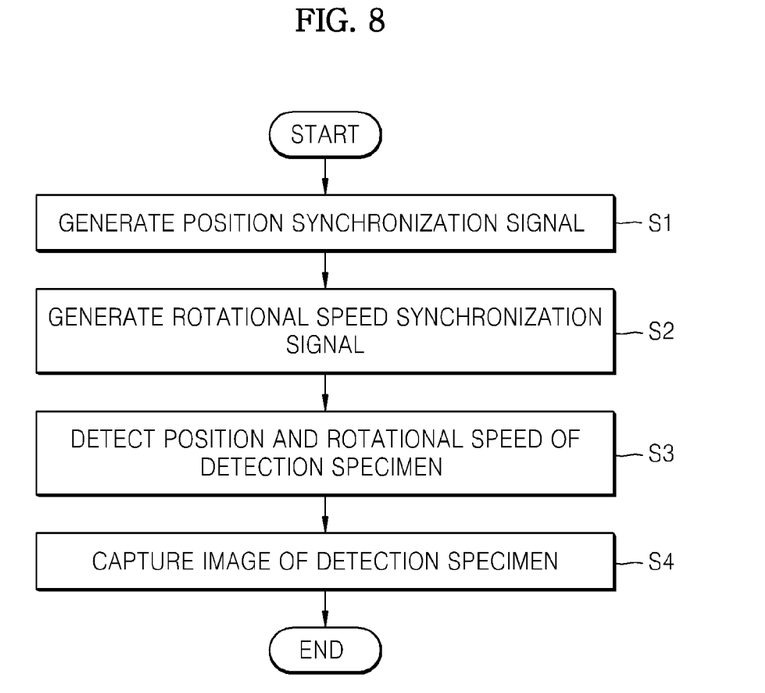
FIG. 8 is a flowchart illustrating a method of checking a state of a rotator according to an embodiment.

FIG. 8 is a flowchart illustrating a method of checking a state of a rotator according to an embodiment of the inventive concept.

Referring to FIG. 8, in operation S1, a position recognition sensor 20 senses a particular position within a rotator 10 based on a recognition mark 80 attached to a rotator 10 to generate a position synchronization signal corresponding to the particular position in the rotator 10, and in operation S2, the position recognition sensor 20 generates a rotational speed synchronization signal having a frequency in proportion to a rotational speed of the rotator 10 by using a rotational speed synchronization signal generating unit 51.

Meanwhile, in operation S3, a control unit 30 detects a position and a rotational speed of a detection specimen existing in the rotator 10 based on the position synchronization signal and the rotational speed synchronization signal, and in operation S4, a camera system 60 captures an image of the detection specimen existing in the rotator 10 based on results of the detection.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A system for checking a state of a rotator, comprising:
    a position recognition sensor that senses a recognition mark attached to rotator at a position and generates a position synchronization signal corresponding to the position of the rotator;
    a control unit that detects a position of a detection specimen existing in the rotator based on the position synchronization signal and generates an image capturing control signal corresponding to the detected position of the detection specimen; and
    a camera system that captures an image of the detection specimen existing in the rotator based on the image capturing control signal.

2. The system of claim 1, further comprising a rotational speed synchronization signal generating unit that generates a rotational speed synchronization signal having a frequency in proportion to a rotational speed of the rotator,
    wherein the control unit detects a position and a rotational speed of a detection specimen existing in the rotator based on the position synchronization signal and the rotational speed synchronization signal and generates an image capturing control signal corresponding to the detected position and the detected rotational speed of the detection specimen.

3. The system of claim 1, wherein the camera system comprises:
an illumination unit that emits light to the detection specimen;
a camera module that captures an image of the detection specimen;
an instrument unit that fixes the camera module;
a supporting unit, to which the instrument unit is connected so that the instrument unit is capable of sliding in a diameter direction of the rotator; and
a feeding motor that transmits motive power to the instrument unit to move the instrument unit.

4. The system of claim 1, wherein at least one chamber, in which a detection specimen is stored, is disposed on a surface of the rotator and the recognition mark that displays data of the chamber is respectively attached on the surface of the rotator, and
the position recognition sensor senses the recognition mark to generate the position synchronization signal.

5. The system of claim 4, wherein the position recognition sensor includes a light emitting unit and a light receiving unit, and the light emitting unit emits light to the recognition mark, and the light receiving unit receives the light that is either reflected by or transmitted through the recognition mark to generate the position synchronization signal.

6. The system of claim 5, wherein the light emitting unit and the light receiving unit are disposed below the rotator and generate the position synchronization signal corresponding to an amount of reflected light.

7. The system of claim 5, wherein the light emitting unit and the light receiving unit are disposed opposite each other, having the rotator interposed therebetween, and generate the position synchronization signal corresponding to an amount of transmitted light.

8. The system of claim 5, wherein the light emitting unit is one of an infrared ray emitter, a light emitting diode (LED), and a laser, and the light receiving unit is a photo-detector.

9. The system of claim 4, wherein the recognition mark includes at least a mark representing an initial start position of the chamber.

10. The system of claim 4, wherein the recognition mark includes at least a mark that represents an image capturing position.

11. The system of claim 4, wherein the recognition mark includes at least a mark that represents a chamber type.

12. The system of claim 4, wherein the recognition mark includes at least one of a initial start position of the chamber, an image capturing position, a chamber type, and the combination thereof.

13. The system of claim 11, the chamber type mark comprises at least a bar.

14. The system of claim 5, the light emitting unit and the light receiving unit are disposed on the same printed circuit board (PCB).

15. The system of claim 5, the light emitting unit and the light receiving unit are disposed on the same side to the rotator.

16. The system of claim 5, the light emitting unit and light receiving unit are disposed in symmetrical configuration.

17. A method of checking a state of a rotator, the method comprising:
sensing a recognition mark attached at a position within a rotator and generating a position synchronization signal corresponding to the position within the rotator;
generating a rotational speed synchronization signal having a frequency in proportion to a rotational speed of the rotator;
detecting a position and a rotational speed of a detection specimen in the rotator based on the position synchronization signal and the rotational speed synchronization signal; and
capturing an image of the detection specimen in the rotator based on results of the detecting.

* * * * *